United States Patent [19]
Horacek

[11] Patent Number: 6,030,642
[45] Date of Patent: Feb. 29, 2000

[54] EXTENDED RELEASE CLONIDINE FORMULATION (CAPSULE)

[76] Inventor: H. Joseph Horacek, 5927 Goldwagon La., Charlotte, N.C. 28227

[21] Appl. No.: 08/884,283

[22] Filed: Jun. 27, 1997

Related U.S. Application Data

[63] Continuation of application No. 08/566,837, Dec. 4, 1995, abandoned, which is a continuation of application No. 08/136,309, Oct. 13, 1993, Pat. No. 5,484,607.

[51] Int. Cl.[7] .............................. A61K 9/64; A61K 9/40; A61K 9/52
[52] U.S. Cl. ........................................... 424/457; 424/456
[58] Field of Search ...................................... 424/460, 457

[56] References Cited

U.S. PATENT DOCUMENTS

| | | | |
|---|---|---|---|
| 3,065,143 | 11/1962 | Christenson et al. | 167/32 |
| 3,427,378 | 2/1969 | Henderson et al. | 424/14 |
| 3,590,117 | 6/1971 | Christenson et al. | 424/19 |
| 3,870,790 | 3/1975 | Lowey et al. | 424/19 |
| 4,094,964 | 6/1978 | Jarrott et al. | 424/1 |
| 4,140,755 | 2/1979 | Sheth et al. | 424/21 |
| 4,167,558 | 9/1979 | Sheth et al. | 424/22 |
| 4,201,211 | 5/1980 | Chandrasekaran et al. | 128/268 |
| 4,226,849 | 10/1980 | Schor | 424/19 |
| 4,259,314 | 3/1981 | Lowery | 424/19 |
| 4,279,928 | 7/1981 | Riley et al. | 424/324 |
| 4,292,303 | 9/1981 | Keith et al. | 424/28 |
| 4,312,878 | 1/1982 | Redmond, Jr. | 424/273 R |
| 4,312,879 | 1/1982 | Lal | 424/273 R |
| 4,357,469 | 11/1982 | Schor | 536/91 |
| 4,369,172 | 1/1983 | Schor et al. | 424/19 |
| 4,505,890 | 3/1985 | Jain et al. | 424/21 |
| 4,540,566 | 9/1985 | Davis et al. | 424/22 |
| 4,556,678 | 12/1985 | Hsiao | 514/652 |
| 4,571,333 | 2/1986 | Hsiao et al. | 424/22 |
| 4,578,264 | 3/1986 | Stricker et al. | 424/37 |
| 4,587,257 | 5/1986 | DeSantis et al. | 514/392 |
| 4,603,141 | 7/1986 | Giles | 514/385 |
| 4,612,008 | 9/1986 | Wong et al. | 604/892 |
| 4,680,186 | 7/1987 | Sheehy et al. | 426/129 |
| 4,685,918 | 8/1987 | Amidon et al. | 604/892 |
| 4,734,285 | 3/1988 | Alderman | 424/468 |
| 4,785,014 | 11/1988 | Goldman-Rakic et al. | 514/401 |
| 4,798,725 | 1/1989 | Patel | 424/456 |
| 4,803,079 | 2/1989 | Hsiao et al. | 424/468 |
| 4,851,228 | 7/1989 | Zentner et al. | 424/456 |
| 4,871,548 | 10/1989 | Edgren et al. | 424/488 |
| 4,874,613 | 10/1989 | Hsiao | 424/458 |
| 4,880,632 | 11/1989 | Lipham et al. | 424/425 |
| 4,883,649 | 11/1989 | Counsell et al. | 424/1.1 |
| 4,894,240 | 1/1990 | Geohegan et al. | 424/497 |
| 4,902,515 | 2/1990 | Loomis et al. | 424/486 |
| 4,931,281 | 6/1990 | Kim et al. | 424/448 |
| 4,946,848 | 8/1990 | Tuttle et al. | 514/282 |
| 4,968,508 | 11/1990 | Oren et al. | 424/468 |
| 4,981,696 | 1/1991 | Loomis et al. | 424/486 |
| 4,994,260 | 2/1991 | Kallstrand et al. | 424/10 |
| 4,996,058 | 2/1991 | Sinnreich | 424/462 |
| 5,002,776 | 3/1991 | Geohegan et al. | 424/497 |
| 5,051,262 | 9/1991 | Panoz et al. | 424/468 |
| 5,082,668 | 1/1992 | Wong et al. | 424/473 |
| 5,133,974 | 7/1992 | Paradissis et al. | 424/480 |
| 5,175,052 | 12/1992 | Tokuda et al. | 428/355 |
| 5,178,868 | 1/1993 | Malmqvist-Granlund et al. | 424/490 |
| 5,209,746 | 5/1993 | Balaban et al. | 604/892.1 |
| 5,212,162 | 5/1993 | Missel et al. | 514/54 |
| 5,212,196 | 5/1993 | House et al. | 514/392 |
| 5,213,808 | 5/1993 | Bar-Shalom et al. | 424/473 |
| 5,221,278 | 6/1993 | Linkwitz et al. | 604/890.1 |
| 5,230,896 | 7/1993 | Yeh et al. | 424/443 |
| 5,275,824 | 1/1994 | Carli et al. | 424/490 |
| 5,484,607 | 1/1996 | Horacek | 424/460 |
| B1 4,389,393 | 10/1985 | Schor et al. | 424/19 |

FOREIGN PATENT DOCUMENTS

| | | | |
|---|---|---|---|
| 0109320 | 5/1984 | European Pat. Off. | A61K 9/26 |
| 0111144 | 6/1984 | European Pat. Off. | A61K 9/24 |

OTHER PUBLICATIONS

Database WPI, Week 8714, Derwent Publications Ltd., London, GB; AN 87–099083 [14] XP002055889 & JP 62 048 618 A (Zeria Shinyaku Kogyo KK) Mar. 3, 1987 (abstract).

Chemical Abstracts, vol. 106, No. 26, Jun. 29, 1987, Columbus, Ohio US; abstract No. 219476; XP002055888 & A.I. Tentsova et al.: "Mechanism of Clofelin Release From Solid Dispersion Systems With Ethyl Cellulose" Farmatsiya, vol. 36, No. 2, – 1987 Moscow, pp. 16–19.

Patent Abstracts of Japan vol. 011, No. 371 (C–462), Dec. 3, 1987 & JP 62 145014 A (Teijin Ltd.), Jun. 29, 1987.

Clonidine in Child and Adolescent Psychiatry, Robert D. Hunt, M.D., Lisa Capper, B.S., and Patricia O'Connell, B.S., Journal of Adolescent Psychopharmacology, vol. 1, No. 1, 1990, pp. 87–102.

Primary Examiner—Peter F. Kulkosky
Attorney, Agent, or Firm—Moore & Van Allen, PLLC; Michael G. Johnston

[57] ABSTRACT

A method of providing a patient needing clonidine with an extended dosage of clonidine over a prolonged period of time. Such method involves administering to the patient an oral dosage unit comprising a homogenous mixture of a therapeutically effective amount of clonidine, about 30 to about 70 percent by weight of one or more cellulose ethers such as hydroxypropyl methylcellulose, and about 30 to about 70 percent by weight of an inert substance such as cornstarch. The oral dosage unit may be contained in a gelatin capsule or in the form of a tablet.

13 Claims, No Drawings

EXTENDED RELEASE CLONIDINE FORMULATION (CAPSULE)

CROSS REFERENCE

This is a continuation of application Ser. No. 08/566,837 filed on Dec. 4, 1995, now abandoned, which is a continuation of Ser. No. 08/136,309, filed Oct. 13, 1993 and now U.S. Pat. No. 5,484,607, the contents of which are incorporated by reference.

Government Rights

None.

BACKGROUND

The present invention relates to an extended release formulation of clonidine. Specifically, it relates to an oral dosage form of clonidine which provides a release period suitable for twice or three times daily dosing while exhibiting good bioavailability.

Clonidine is a well known and widely used alpha-adrenergic agonist. Clonidine is effective in the treatment of a wide range of clinical disorders including hypertension; prophylaxis of common migraine headaches; subduing motor tics such as in Tourette's syndrome; and decreasing hyperactivity, impulsivity and over excitability in Attention Deficit Hyperactivity Disorder, manic states and many other clinical syndromes which involve over arousal.

Clonidine is given in either an oral dose in tablet form three to four times per day or via a transdermal patch. In the oral formulation currently in use, clonidine is almost completely absorbed from the gastrointestinal tract, but it is subject to rapid liver metabolism. The biological half-life ranges from about four to six hours after oral administration, with wide interpatient variability.

The traditional oral formulations of clonidine have disadvantages. The oral dose has the main side-effect of sedation, particularly about an hour after the given dose when the patient may become transiently sedated, even falling asleep. Because the half-life of this dosage form of clonidine is only about four to six hours, there is also the problem of the drug wearing off with some rebound hyperarousal. This can occur in the middle of the night causing insomnia, and even nightmares in some cases. Such side effects have limited the practical usefulness of oral clonidine.

A transdermal patch has partially solved these problems by providing a more stable serum level (U.S. Pat. No. 4,201,211). The transdermal patch, however, has the disadvantage of producing a high rate of contact dermatitis. There are also problems with patch adherence to the skin in humid environments and with active individuals. The patch may need replacement after extended swimming or exertion. The inconvenience of the patch can lead to reduced patient compliance.

For the foregoing reasons, there is a need for a clonidine formulation which is capable of stable therapeutic effects by maintaining a constant serum level for an extended period in order to avoid the "peak and trough" side effects of transient sedation at peak serum levels and rebound exacerbation of symptoms at trough levels. The clonidine formulation should be easy and inexpensive to manufacture and convenient for the patient to use.

SUMMARY

The present invention is directed to an extended release clonidine formulation which satisfies these needs. The present invention comprises an oral extended release dosage formulation comprising a homogenous mixture of a therapeutically effective amount of clonidine; from about 30 to about 70 percent by weight of one or more cellulose ethers, such as hydroxypropyl methylcellulose; and from about 30 to about 70 percent by weight of a therapeutically inert, pharmaceutically acceptable adjunct material such as cornstarch, as well as a method of administering an extended release formulation of clonidine to effect central alpha-adrenergic stimulation over a prolonged period of time for patients suffering from any condition which clonidine may benefit.

Clinical studies of an embodiment of the present invention yielded surprisingly effective and unanticipated results. The oral extended release dosage unit formulation of the present invention appeared to cause a sustained release of clonidine over a prolonged period of time. The side effects of transient sedation and rebound hyperarousal were overcome. Thus the present invention overcomes the "peak and trough" side effects of the traditional oral clonidine formulations to provide more stable therapeutic effects. Furthermore, the extended release clonidine formulation is more convenient to use than the transdermal patch thereby resulting in improved patient compliance.

Of particular importance is the ease with which the capsule can be manufactured. It does not require elaborate and expensive equipment and can be prepared quickly and inexpensively in a local pharmacy from ordinarily available materials by any pharmacist properly instructed in its preparation.

These and other features, aspects, and advantages of the present invention will become better understood with reference to the following description and appended claims.

DESCRIPTION

In accordance with the present invention, a formulation for the extended release of clonidine is provided. The extended release formulation of the present invention is preferably an oral dosage unit comprising a homogenous mixture of clonidine, one or more cellulose ethers, and one or more therapeutically inert, pharmaceutically accepted fillers.

Clonidine is a 9-carbon, two-ringed imidazoline derivative. As used herein, the term "clonidine" denotes generally one or more of 2,6-dichloro-N-2-imidazolidinylidene benzeneamine, or benzeneamines structurally and functionally related thereto that are described in U.S. Pat. No. 3,454,701. U.S. Pat. No. 3,454,701 is incorporated herein by reference for its disclosure of such structurally and functionally related benzeneamines. With respect to the preferred embodiments of the present invention, the term "clonidine" denotes 2,6-dichloro-N-2-imidazolidinylidene benzeneamine.

Polymeric compositions have been widely used as a matrix for extended or sustained drug release formulations. For such applications, a highly hydrophilic polymeric composition is suitably employed. Cellulose ethers such as methyl cellulose and hydroxypropyl methylcellulose are among the polymeric compositions which have been most widely used in this manner. Other cellulose ethers, such as ethyl cellulose, methyl cellulose, hydroxypropyl cellulose, hydroxyethyl cellulose, sodium carboxymethyl cellulose, have also been used. They exhibit fast hydration forming a protective initial gel layer quickly through which the drug is released to the system. Once the initial gel layer is formed, it continues to allow additional water to penetrate into the mass. Soluble materials will wet, dissolve, and diffuse out of the matrix while insoluble materials will be held in place until the surrounding complex erodes or dissolves away. As the outer gel layer begins to fully hydrate and be dissolved, a new layer replaces it that is tight and strong enough to retard diffusion and sustain uniform drug release. Factors affecting the rate of hydration of the polymeric composition, and thereby the drug release rate, include its viscosity, concentration, particle size, and chemical makeup.

Another factor affecting the rate of gel formation or hydration of the polymeric composition used as an extended drug release matrix is the chemical characteristics of the drug employed. Certain polymers can be employed effectively for some drugs but not for others. The degree of water solubility of the drug, molecular weight of the drug, and the diffusion coefficient of the drug in hydrated polymer are critical.

The oral dosage unit of the embodiments of the present invention also contain one or more compositions such as diluents or fillers which are therapeutically inert and pharmaceutically acceptable and provide bulk. Examples of such diluents or fillers include cornstarch, lactulose, dextrose and the like.

The oral dosage unit can be in the form of a tablet or a capsule. Tablets may be prepared or manufactured in accordance with an embodiment of the present invention on any conventional tableting equipment. Where the oral dosage unit is in the form of a capsule, the capsule may be any standard two-piece gelatin capsule of sufficient size for containing the formulation.

In the preparation of the oral extended release formulation of the present invention, clonidine tablets are ground into a fine powder and mixed with one or more cellulose ethers and one or more diluents or fillers and either tableted or inserted into a gelatin capsule. The amount of clonidine that is included per oral dosage unit may vary widely. The therapeutically effective dose range of about 0.025 mg to about 0.40 mg per unit is preferred to control most of the symptoms of the clinical disorders listed above which clonidine may benefit. The dose of the oral dosage unit can be exactly specified, however, as required.

The cellulose ethers or mixtures thereof employed as the extended release matrix in the present invention are ultra-fine, rapidly hydrating formulations having a number average molecular weight of at least 86,000 or a 2% aqueous solution of viscosity of at least 4000 cps and wherein at least 90% by weight of the cellulose ether particles can pass through a 100 mesh screen. An important aspect of the present invention is that the extended release profile of clonidine can be specified by the types or amounts of cellulose ethers used. The invention is thus very adaptable and versatile to each particular use. The oral dosage formulation herein described provides a preferred release period suitable for the dosing of clonidine twice per day, at twelve hour intervals.

A functionally effective amount of the cellulose ether composition is employed. Such an amount is an amount sufficient to extend the release of clonidine for up to twelve hours. Such an amount can vary and typically ranges from about 30 to about 70 weight percent, and preferably from about 30 to about 40 weight percent based on the weight of the capsule, although any functionally effective amount can be employed.

The preferred extended release matrix is hydroxypropyl methylcellulose such as Methocel®, which is manufactured by the Dow Chemical Company, U.S.A. The preferred Methocel® for an eight hour release period is E4M which has a hydroxypropoxyl substitution of from about 7 to about 12 weight percent, a methoxyl substitution of from about 28 to about 30 weight percent, a number average molecular weight of about 86,000, a 2% aqueous solution of viscosity of about 4000 cps and 95% by weight can pass through a 100 mesh screen. The preferred Methocel® for a twelve hour release period is K100M which has a hydroxypropoxyl substitution of from about 7 to about 12 weight percent, a methoxyl substitution of from about 19 to about 24 weight percent, a number average molecular weight of about 246,000, a 2% aqueous solution of viscosity of about 100,000 cps and at least 90% by weight can pass through a 100 mesh screen.

Diluents and fillers, such as cornstarch, lactulose, dextrose and the like, are included in the preparation of the present invention from about 30 to about 70 weight percent based on the weight of the capsule.

The present invention should be used for the exact same indications as other forms of clonidine. The optimal dose is related to weight and age, as well as other factors such as the rate of biotransformation in the liver which can be quite variable among patients. Doses must therefore be individualized in each case by empiric trials. The best way to find the optimal dose of clonidine according to the embodiments of the present invention is to increase the dose slowly and to monitor the therapeutic effects and side effects. If the patient becomes sedated or paradoxically irritable with an increase in dose, then it is advisable to reduce the dose to that previously well-tolerated, hold at this dose for several weeks and then advance again as tolerated. To minimize sedation it is best to start with a very low dose, 0.025 mg. every twelve hours is preferred, and to work up at weekly intervals in increments of 0.025 mg. Clonidine tends to work better after longer use with additional benefits evident even after many months.

The previously described aspects of the present invention have many advantages, particularly the minimization of the side effects of the traditional oral clonidine formulation. As a result of the extended delivery of the drug, the formulation of the present invention is capable of maintaining a constant level of clonidine in the blood thereby avoiding the side effects of transient sedation and hyperarousal and providing more stable therapeutic effects. Twice or three times daily dosages are all that is required. The extended release clonidine formulation of the present invention is also more convenient to use than the transdermal patches thereby resulting in better patient compliance. The embodiments of the present invention are easily manufactured by a trained pharmacist properly instructed in its preparation without elaborate and expensive equipment.

Clonidine has been found to be very useful in aiding the onset of sleep in Attention Deficit Hyperactivity Disorder patients. Such patients often have a lifetime history of difficulty getting to sleep. This difficulty with state regulation appears to be part of the Attention Deficit Hyperactivity Disorder complex of symptoms. The sedation experienced approximately one hour after the traditional oral tablet dose of clonidine which is troublesome in the day is often very useful at night in aiding the onset of sleep. One difficulty in a significant number of patients is the problem of waking about four to six hours later, sometimes with a nightmare. This rebound hyperarousal can limit the use of clonidine for this purpose.

The present invention, with its slow release, has proven to be free of this problem. On the other hand, because of its slower onset of action it does not aid in the onset of sleep as effectively as the tablet form. One effective strategy is to give a formulation according to the present invention earlier in the evening, at 5 p.m., for example, to allow several hours for the onset of the effect. Another strategy which has proven very effective is to give a traditional oral tablet dose of clonidine, containing about 0.05 mg. to about 0.2 mg. clonidine, with the extended release formulation of the present invention containing about 0.05 mg. to about 0.2 mg. of clonidine. The tablet aids in the onset of sleep and the extended release form maintains an adequate level of medication throughout the night, thus preventing the "middle of the night" wakening and nightmare problems.

Experience has shown that the foundation of all mental health must begin with an adequate night's rest. Regulating sleep and wakefulness along with a safe, non-habit forming medication has often proven very valuable in controlling adverse symptoms in the day such as inattention, distractibility, and irritability.

The following non-limiting example serves to further illustrate the invention:

EXAMPLE

This example shows how to manufacture 100 units of an oral extended release formulation of clonidine in capsule form containing about 0.025 mg. of clonidine in either eight or twelve hour release formulations.

Powdered clonidine is prepared by grinding twenty five 0.1 mg. clonidine tablets, then sifting the powder through a fine, 100 mesh screen to ensure small particle size. The powdered clonidine is mixed with 7 gm. of Methocel® K100M for 12 hour release or Methocel® E4M for 8 hour release. Cornstarch or lactulose is added until the total weight of the mixture equals 20 gm. The resulting mixture is homogenized by shaking and divided equally among 100 gelatin capsules each weighing about 0.20 gm.

The above formulation was clinically tested in 50 patients in which clonidine had previously proved effective but side effects of sedation via the oral tablet route, or contact dermatitis via the transdermal patch, had limited its usefulness. By starting at doses at or below the tablet form, the risk of the drug not releasing at all resulting in no therapeutic effect, or the drug releasing too fast approximating the release of the tablet form, was minimized. Optimal doses of clonidine ranged from about 0.025 mg. to about 0.15 mg. every 12 hours.

The results of the clinical tests yielded surprising and unanticipated results. The extended release capsule appeared as effective as the tablet or transdermal patch while producing significantly fewer side effects such as hyperarousal, contact dermatitis, and sedation. The twice or three times daily dosages proved more convenient for the patient and resulted in greater patient satisfaction and better compliance.

Although the present invention has been described in considerable detail with reference to certain preferred versions thereof, other versions are possible. For example the extended release formulation of the present invention is effective when the drug to be delivered is methylphenidate or dextroamphetamine. The spirit and scope of the appended claims should not be limited to the description of the preferred versions contained herein.

I claim:

1. An oral pharmaceutical dosage unit formulation for the extended release of clonidine to effect central alpha-adrenergic stimulation over a prolonged period upon administration thereof, wherein the oral dosage unit is a gelatin capsule containing a homogeneous powder mixture, the homogenous mixture consisting essentially of:
   a. from about 0.025 mg. to about 0.40 mg. clonidine for the treatment of attention deficit hyperactivity disorder;
   b. from about 30 to about 70 percent by weight of a high molecular weight, high viscosity cellulose ether; and
   c. a therapeutically inert, pharmaceutically acceptable adjunct material, wherein the release period is from about 8 to about 12 hours.

2. The extended release clonidine formulation according to claim 1, wherein the capsule comprises from about 30 to about 40 percent by weight of the cellulose ether.

3. The extended release clonidine formulation according to claim 1, wherein the cellulose ether is selected from the group consisting of ethyl cellulose, methyl cellulose, hydroxypropyl cellulose, hydroxypropyl methylcellulose, hydroxyethyl cellulose, sodium carboxymethyl cellulose, and mixtures thereof.

4. The extended release clonidine formulation according to claim 1, the cellulose ether having a number average molecular weight of at least 30,000.

5. The extended release clonidine formulation according to claim 1, wherein the cellulose ether has a 2% aqueous solution of viscosity of at least 4000 cps.

6. The extended release clonidine formulation according to claim 3, wherein the hydroxypropyl methylcellulose has a hydroxypropoxyl substitution of from about 7 to about 12 weight percent, a methoxyl substitution of from about 28 to about 30 weight percent, a number average molecular weight of about 86,000, a 2% aqueous solution viscosity of about 4000 cps.

7. The extended release clonidine formulation according to claim 3, wherein the hydroxypropyl methylcellulose has a hydroxypropoxyl substitution of from about 7 to about 12 weight percent, a methoxyl substitution of from about 19 to about 24 weight percent, a number average molecular weight of about 246,000, a 2% aqueous solution viscosity of about 100,000 cps.

8. The extended release clonidine formulation according to claim 1, wherein the amount of therapeutically inert, pharmaceutically acceptable adjunct material is from about 30 to about 70 percent by weight.

9. The extended release clonidine formulation according to claim 1, wherein the therapeutically inert, pharmaceutically acceptable adjunct material is cornstarch.

10. The extended release clonidine formulation according to claim 1, wherein the therapeutically inert, pharmaceutically acceptable adjunct material is lactulose.

11. The extended release clonidine formulation according to claim 1, wherein the therapeutically inert, pharmaceutically acceptable adjunct material is dextrose.

12. A method for effecting central alpha-adrenergic stimulation over a prolonged period in a mammalian specie which comprises administering the extended release clonidine formulation as defined in claim 1.

13. The extended release clonidine formulation according to claim 1, wherein the release rate is one that provides attention deficit hyperactivity disorder therapy.

* * * * *

UNITED STATES PATENT AND TRADEMARK OFFICE
CERTIFICATE OF CORRECTION

PATENT NO. : 6,030,642
DATED : February 29, 2000
INVENTOR(S) : H. Joseph Horacek It is certified that error appears in the above-identified patent and that said Letters Patent is hereby corrected as shown below:

In the claims:
Please cancel claim 13.

Signed and Sealed this

Ninth Day of January, 2001

Attest:

Q. TODD DICKINSON

Attesting Officer

Commissioner of Patents and Trademarks